United States Patent [19]

Thomas

[11] Patent Number: 5,637,292
[45] Date of Patent: Jun. 10, 1997

[54] WATER BASED UV CURABLE NAIL POLISH BASE COAT

[75] Inventor: Bradley R. Thomas, Santa Ana, Calif.

[73] Assignee: Bradley Ray Thomas, Santa Ana, Calif.

[21] Appl. No.: 518,636

[22] Filed: Aug. 24, 1995

[51] Int. Cl.[6] ....................................... A61K 7/04
[52] U.S. Cl. ....................................... 424/61
[58] Field of Search ....................................... 424/61

[56] References Cited

U.S. PATENT DOCUMENTS

| | | | |
|---|---|---|---|
| 4,345,058 | 8/1982 | Dettling | 528/48 |
| 4,596,260 | 6/1986 | Giuliano | 424/61 |
| 4,704,303 | 11/1987 | Cornell | 424/61 |
| 4,818,520 | 4/1989 | Fleischner | 424/61 |
| 4,855,184 | 8/1989 | Klun | 424/425.1 |
| B1 4,596,260 | 7/1988 | Giuliano | 424/61 |

*Primary Examiner*—Peter F. Kulkosky

[57] ABSTRACT

The product invention entitled as water based UV curable human nail coating is the result of years of experience, research and testing. The formula is as follows: aliphatic waterborne urethane containing 40% solids in water with N.N-Diethylethanamine, acrylated urethane containing 50% polymer of alkyl carbomonocycle diisocyanate with alkane-polyol polyacrylates and 50% acrylated polyol, isopropanol, propylene glycol methyl ether acetate, 2-hydroxy-2-methyl-1-phenyl-1-propanone, hydrolyzed keratin @ 125,000 molecular weight 13% solids in water with 2% propylene glycol, protein hydrolyzate from milk. These ingredients are placed in a plastic mixing container in the given order then thoroughly mixed for 10 minutes or until all visible lumps and droplets are no longer visible.

1 Claim, No Drawings

WATER BASED UV CURABLE NAIL POLISH BASE COAT

FIELD OF THE INVENTION

A transluscent, milky, low viscosity, water based, U.V. curable polymer/monomer emulsion/solution blend designed for the use as a human nail coating.

INVENTION DESCRIPTION

This product, which is believed to be the first of its kind for its use as a human finger and toe nail polish base coating, is a waterbased, ultra-violet light curable, urethane acrylic hybrid emulsion system. It consists of a urethane acrylic copolymer/emulsion/solution containing a tertiary amine, blended with art acrylate monomer, low molecular weight keratin solution, hydrated milk protein, isopropanol as a co-solvent, a glycol ether acetate as a coalescent and a free radical photoinitiator. This mixture is thoroughly blended with a stainless steel mixer blade at 100–200 rpm until all visible partially miscible droplets are solvated to a stable emulsion. This product is then dispensed by syringe into individual amber glass bottles then sealed with a polypropylene cap of matching threads along with the appropriate length nail brush.

The product is applied in a thin coating. It is allowed to dry under forced warm air for one minute, the coating is then subjected to ultra-violet light in the range of 260–380 nanometers in wavelength and 5–100 milliwatts/square centimeter in intensity for 10 seconds to 3 minutes to crosslink the polymer. The coating then becomes a durable, chemically resistant, infusible and abrasion resistant solid coating.

I claim:

1. A water-based, UV curable composition for coating human nails, comprising a urethane acrylic copolymer emulsion, tertiary amine, low molecular weight keratin solution, free radical photoinitiator, acrylic polymer, acrylate monomer, hydrated milk protein and either isopropanol or glycol ether acetate, said coating being fast dry/cure, durable, nail strengthening, acetone resistant, hypoallergenic and low odor.

* * * * *